United States Patent [19]
Sanghera et al.

[11] Patent Number: 6,157,856
[45] Date of Patent: Dec. 5, 2000

[54] TISSUE DIAGNOSTICS USING EVANESCENT SPECTROSCOPY

[75] Inventors: Jasbinder Sanghera, Burke; Ishwar D. Aggarwal, Springfield, both of Va.

[73] Assignee: The United States of America as represented by the Secretary of the Navy, Washington, D.C.

[21] Appl. No.: 09/313,577

[22] Filed: May 12, 1999

[51] Int. Cl.$^7$ ........................................ A61B 5/00
[52] U.S. Cl. ............................................. 600/478
[58] Field of Search ............................ 600/473, 478

[56] References Cited

PUBLICATIONS

Article entitled "Diagnostics of cancer by fiberoptic evanescent wave FITR (FEW–FITR) spectroscopy" by Afanasyeve et al and published in SPIE in 1996.

Article entitled "Detection of Spectral differences between normal and cancerous tissue using near–infrared spectroscopy" by Cooney et al and published in BTuA2–1/67 probably in 1967.

Article entitled "MIR–fiber spectroscopy for minimal invasive diagnostics" by Artjushenko et al and published in SPIE in.

Article entitled "Infrared fibers:power delivery and medical applications" by Artjushenko et al and published in SPIE in 1995.

*Primary Examiner*—William E. Kamm
*Attorney, Agent, or Firm*—John J. Karasek; George A. Kap

[57] ABSTRACT

A method for in-vivo analysis of a biomedical sample characterized by contacting the sample with a chalcogenide glass fiber directly or through a crystal or other medium, with the chalcogenide fiber having input and output ends and light transmitted thereby with some of the light leaving the fiber to form evanescent field, which fiber transmits a signal in response to absorption of some of the light in the evanescent field by the sample, and processing the signal with a Fourier Transform IR Spectrometer to obtain a spectrum which indicates surface character of the sample without water masking the signal.

20 Claims, 8 Drawing Sheets

TISSUE DIAGNOSTICS USING EVANESCENT SPECTROSCOPY

BACKGROUND OF THE INVENTION

1. Field of the Invention

This invention pertains to evanescent spectroscopic analysis of biomedical samples, particularly flesh and organs, using chalcogenide glass fibers.

2. Description of Related Art

There is significant interest in the medical community for non-invasive and minimal-invasive medical diagnostic techniques using fiber optics. Silica based fibers have been used in biomedical applications for a considerable time for performing laser surgery, visible examination by endoscope and such, as well as sensing and analysis using biochemical compounds such as enzymes and antibodies. Since silica fibers transmit between the near ultraviolet and about 2 microns, the analysis is limited. For example, many biomedical samples have important identifying indicia beyond about 2 microns. Wavelengths at about 3 microns or 6.4 microns, correspond to the OH stretching absorption and the Amide II (N-H stretching vibration) absorption in proteins, respectively. This problem of insufficient transmission is further compounded by the fact that 6.45 micron wavelength is absorbed by the atmosphere and precautions must be taken to minimize atmospheric absorption over long path lengths. In the case of cancerous tumors or unidentified foreign inclusions, it has been the practice that the appropriate section was usually removed from the body, sliced into a thin section, desiccated and then characterized using optical microscopy. More recently, thin sections have been characterized using infrared spectroscopy whereby cancer cells have exhibited unique and characteristic special features in the 2–12 micron wavelength region. The chalcogenide glass fibers transmit in the 2–12 micron wavelength region which coincides with the wavelength region of importance in biomedical spectroscopy. Therefore, chalcogenide fibers can be used for infrared spectroscopy. Furthermore, these fibers should be well suited for non-invasive spectroscopy and identification by enhancing spectroscopic analysis of human and animal flesh, tissue and human organs.

The articles entitled "Diagnostics of cancer by fiberoptic evanescent wave FTIR (FEW-FTIR) spectroscopy" by Afanasyeva et al published in 1996 in vol. 2928 of SPIE; "Detection of spectral differences between normal and cancerous oral tissue using near-infrared spectroscopy" by Cooney et al believed to be published in 1998 in Btu A 2-1/67; "MIR - fiber spectroscopy for minimal invasive diagnostics" by Artjushenko et al published in 1995 in vol. 2631 of SPIE; and "Infrared fibers: power delivery and medical applications" by Artjushenko et al published in 1995 in vol. 2396 of SPIE, are pertinent hereto and relate generally to evanescent spectroscopy and to detection of cancerous tissues.

OBJECTS AND BRIEF SUMMARY OF THE INVENTION

An object of this invention is to analyze a biomedical sample by means of evanescent spectroscopy.

Another object of this invention is to spectroscopically analyze a biomedical sample without desiccating same.

Another object of this invention is to spectroscopically analyze a biomedical sample at a point that is remote from where the sample is located.

These and other objects of the invention can be achieved by contacting the biomedical sample with a chalcogenide glass fiber and characterizing same by evanescent spectroscopy.

DETAILED DESCRIPTION OF THE INVENTION

Figure 1:
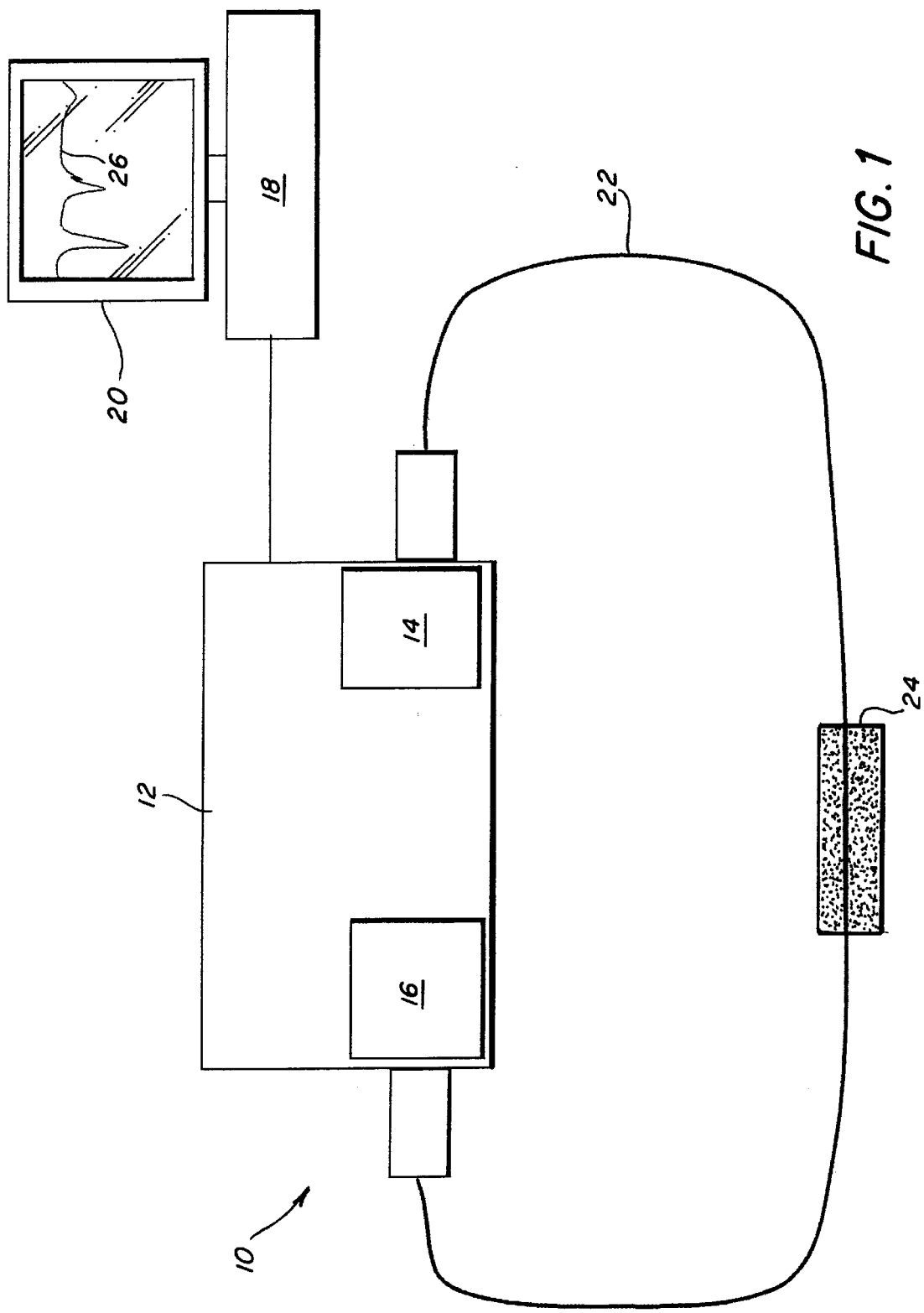
FIG. 1 is a schematic of the experimental setup used in the examples herein.

This invention pertains to a method for evanescent spectroscopic analysis of a biomedical sample that needs not be desiccated by the use of a chalcogenide glass fiber that can transmit over the range of about 2–12 microns. More specifically, the method includes the steps of contacting the sample and detecting by evanescent spectroscopy any absorption by the sample in order to determine characteristics of the sample at the contact area.

This invention relates particularly to in-vivo analysis of human and non-human tissues and organs which can be living or non-living.

The glass fiber contact with the sample is a critical step since it allows a portion of the evanescent light traveling through the multimode fiber to be absorbed by the sample. What is absorbed by the sample on contact with the fiber are discrete wavelengths of the light in the evanescent field of the fiber. Then a detector, such as an FTIR detector with a Nichrome wire light source, is used to determine what wavelengths of the light were absorbed. The light wavelengths absorbed by the sample are not significantly absorbed by water in the sample since the evanescent field penetration into the sample is not deep enough to be completely absorbed by water. It is estimated that the evanescent field penetration is about 1–11 microns in thickness. Therefore, water absorption bands do not mask the infrared spectrum. Unlike prior art, where thin sample sections had to be desiccated before recording the infrared transmission spectrum, this disclosure does not require desiccation of the sample.

Instead of the fibers directly contacting the sample, means in the form of a crystal or other glass which transmits in a similar wavelength region, can be interposed between fiber ends and the sample. In this situation, the means is directly in contact with the sample and is responsible for the evanescent coupling the sample. For example, one fiber group conveys light from a light source through a crystal or glass in contact with the sample whereas another fiber group conveys non-absorbed light after evanescent coupling from the crystal or glass to a detector.

The contact between the fiber and the sample relies on absorption of the evanescent field by the sample. The absorption signal can be improved by prolonging the contact time to improve the signal/noise ratio. Also, the signal can be improved by increasing the contact distance, however, this approach can reach a point of no benefit since the evanescent field is depleted as the contact distance is increased. Although contact time on the order of a fraction of a minute, such as one half of one minute, can be used, time to record a spectrum of a sample can be instantaneous. As for contact distance, typically 2–20 cm is sufficient, since beyond about 20 cm, no significant benefit is realized. The signal can also be improved by tapering the fiber to a smaller diameter over the contact length, which signal can now be increased due to excitation of higher order modes and, therefore, producing more evanescent light for coupling to the sample.

The light that can be introduced into the fiber can come from any light source. Typically, it is monochromatic light from a laser or a broadband light from a glow bar or filament which can be provided within a spectrometer. The detector can also be a part of the spectrometer.

Refractive index of the glass fiber core is typically high in order to retain substantially all of the light transmitted by the fiber within the core. A typical chalcogenide fiber core has refractive index on the order of 2.8. However, some of the light in the core leaves the core and this light outside of the core is used for chemical detection by evanescent wave spectroscopy.

The fiber used herein is typically multimode although a singlemode fiber can be also used. The multimode fiber can carry more light than a singlemode fiber because it is larger and for that reason is typically used since the evanescent field is stronger in a multimode fiber due to the fact that more light is accommodated.

The glass fibers typically used herein are chalcogenide multimode cladless glass fibers, which includes chalcohalide fibers, of a diameter typically 25–1000 microns, more typically 50–500 microns. Chalcogenides glasses, from which the fibers can be drawn, include at least one of the chalcogenide elements of sulfur, selenium or telurium and typically include at least one of Ge, As, Sb, Ti, Pb, Ba, Si, P, Ga, In, Cl, Br, and I. Such glasses can also contain one or more rare earth elements. Chalcogenide glasses typically contain at least 25 mole %, and more generally at least 50 mole %, of one or more of three chalcogenide elements.

Suitability of the chalcogenide glasses for purposes herein is primarily due to the fact that the fibers made from the glasses transmit in the "fingerprint" region of about 2–12 microns where practically all molecular species possess characteristic infrared vibrational bands. The chalcogenide glasses have certain other advantages. The low phonon energy chalcogenide glasses, of phonon energy of less than 350 $cm^{-1}$, are excellent host materials for rare earth doping. Fluoresense and laser transitions beyond 2 microns are possible in these materials which might not be seen in other energy phonon host materials due to multiphonon absorption.

Also, cladless fibers or fibers without cladding are typically used in order to capture a portion of the evanescent field which forms on the outside of the fiber core. A cladding on the core of a fiber will preempt the evanescent field, or most of it, depending on thickness of this cladding. For that reason, fibers without cladding in the region used for evanescent coupling are typically used in order to characterize the sample in contact with the fiber by evanescent spectroscopy. The cladding can be thick enough to prevent evanescent absorption over the length of the fiber but can be completely or partially removed from the specific length desired for evanescent coupling. The glass clad fibers can also be tapered in the evanescent coupling region to a smaller diameter thus exciting higher order modes over the contact length for good evanescent coupling to the sample.

Having described the invention, the following examples are given to illustrate specific applications of the invention including the best mode now known to perform the invention. These specific examples are not intended to limit the scope of the invention described in this application.

EXAMPLE 1

This example demonstrates evanescent infrared spectra recorded when chicken parts were placed on a chalcogenide fiber. The experimental setup used herein is shown schematically in FIG. 1 where the setup 10 includes Fourier Transform infrared (FTIR) spectrometer 12, which includes Nichrome wire light source 14 and detector 16. Spectrometer 12 is connected to computer 18 which in turn, is connected to monitor 20. Light source 14 is connected to the input end a chalcogenide fiber 22 which winds through evanescent test area 24 and the output end of chalcogenide fiber 24 is connected to detector 16 of the FTIR spectrometer 12. The evanescent spectra 26 of the sample is recorded on monitor 20. The surface contact between the sample and fiber 22 takes place in evanescent test area 24 where the sample absorbs certain wavelengths of light propagating through the fiber and the detector detects the absorbed wavelengths and, with the aid of the spectrometer and the computer, displays it as a spectrum of the sample at the point of contact with the sample.

Approximately 1 meter of a multimode telluride glass fiber was used in this example. The fiber had composition of $Ge_{30} As_{10} Se_{30} Te_{30}$, had diameter of 250 microns, and was unclad. The fiber ends were cleaved and then terminated using standard SMA connectors. Light from the spectrometer was injected into the input of the fiber at the light source of the spectrometer using focusing optics. The output end of the fiber was connected to the liquid nitrogen cooled MCT detector also using focusing optics. The input and output ends were aligned so as to maximize the throughput signal. Subsequently, samples of chicken breast, fat, skin, liver and bone were sequentially placed on top of about an 8-cm length of the fiber in the evanescent test are and the evanescent infrared spectrum was recorded for each chicken part individually using a resolution of 4 $cm^{-1}$. The time taken to record all of the spectra for the chicken parts was kept constant at 30 seconds each. For comparison purposes, the spectrum of water was also recorded with the chalcogenide fiber.

Figure 2:
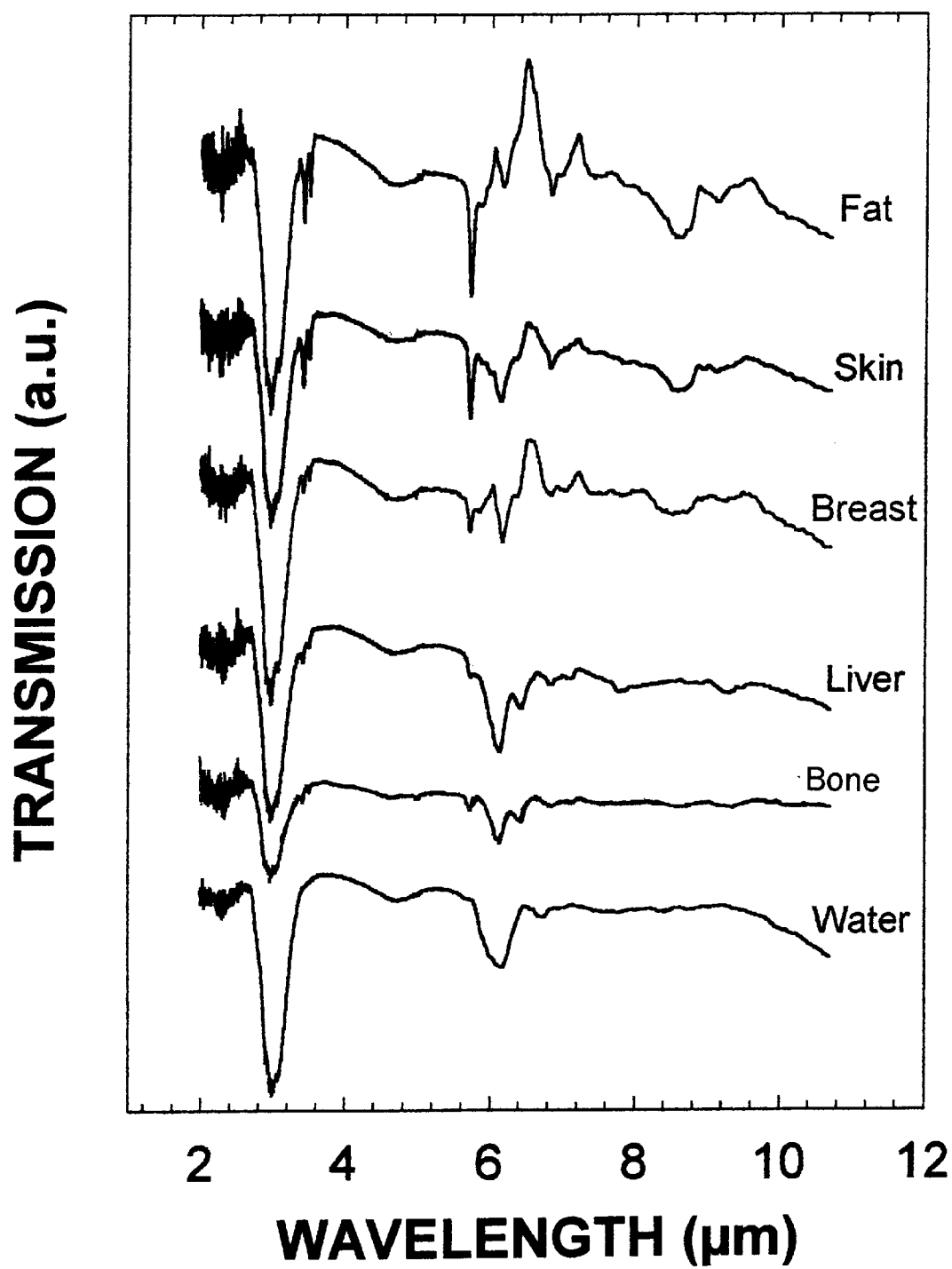
FIG. 2 shows the compilation evanescent spectra of chicken parts and water between about 2 and 12 microns.
Figure 3A:
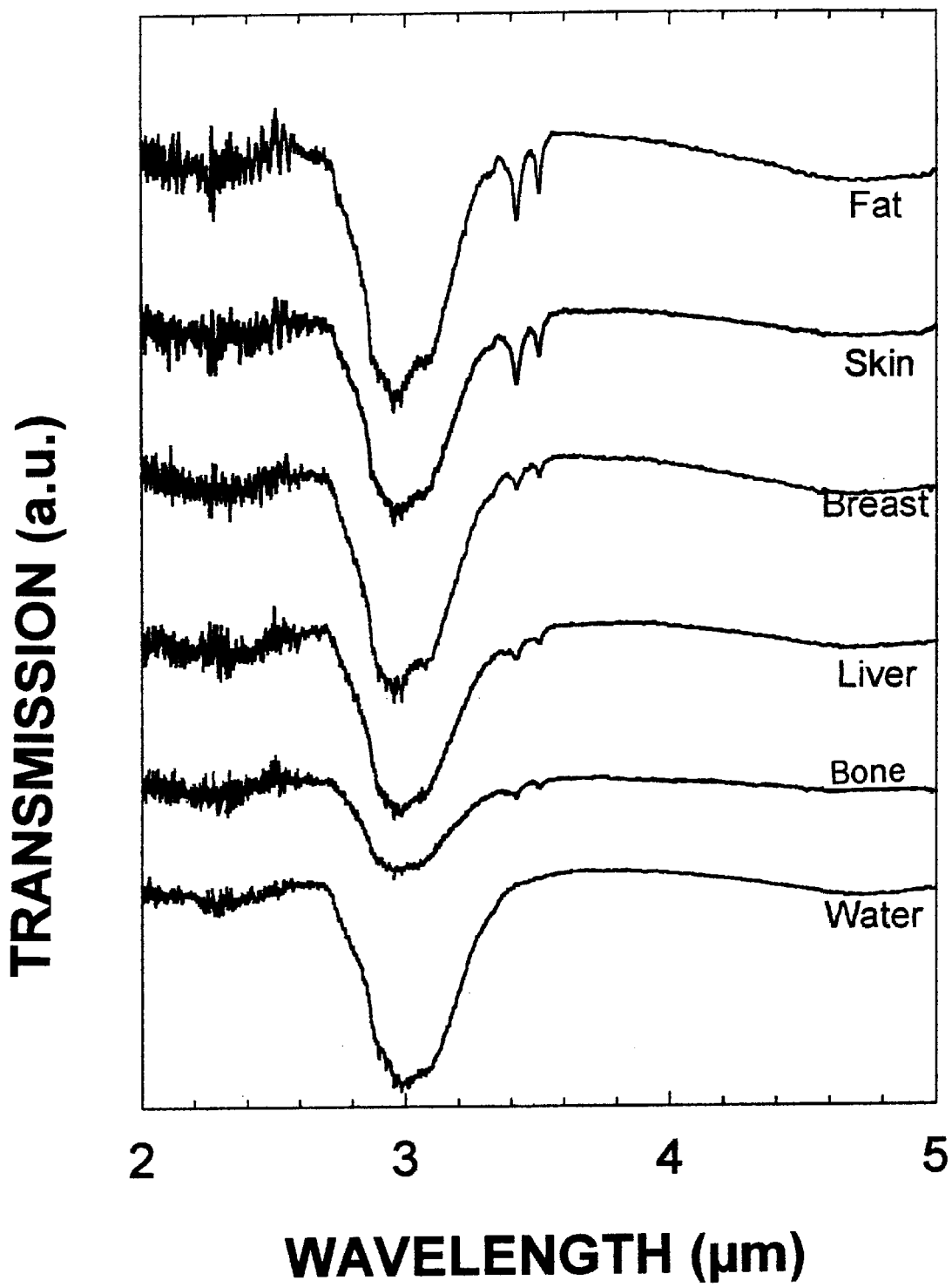
FIGS. 3a, b, and c show the same data as in FIG. 2 but enlarged over wavelength regions of 2–5 microns, 5.5–7 microns, and 7–10 microns, respectively.
Figure 3B:
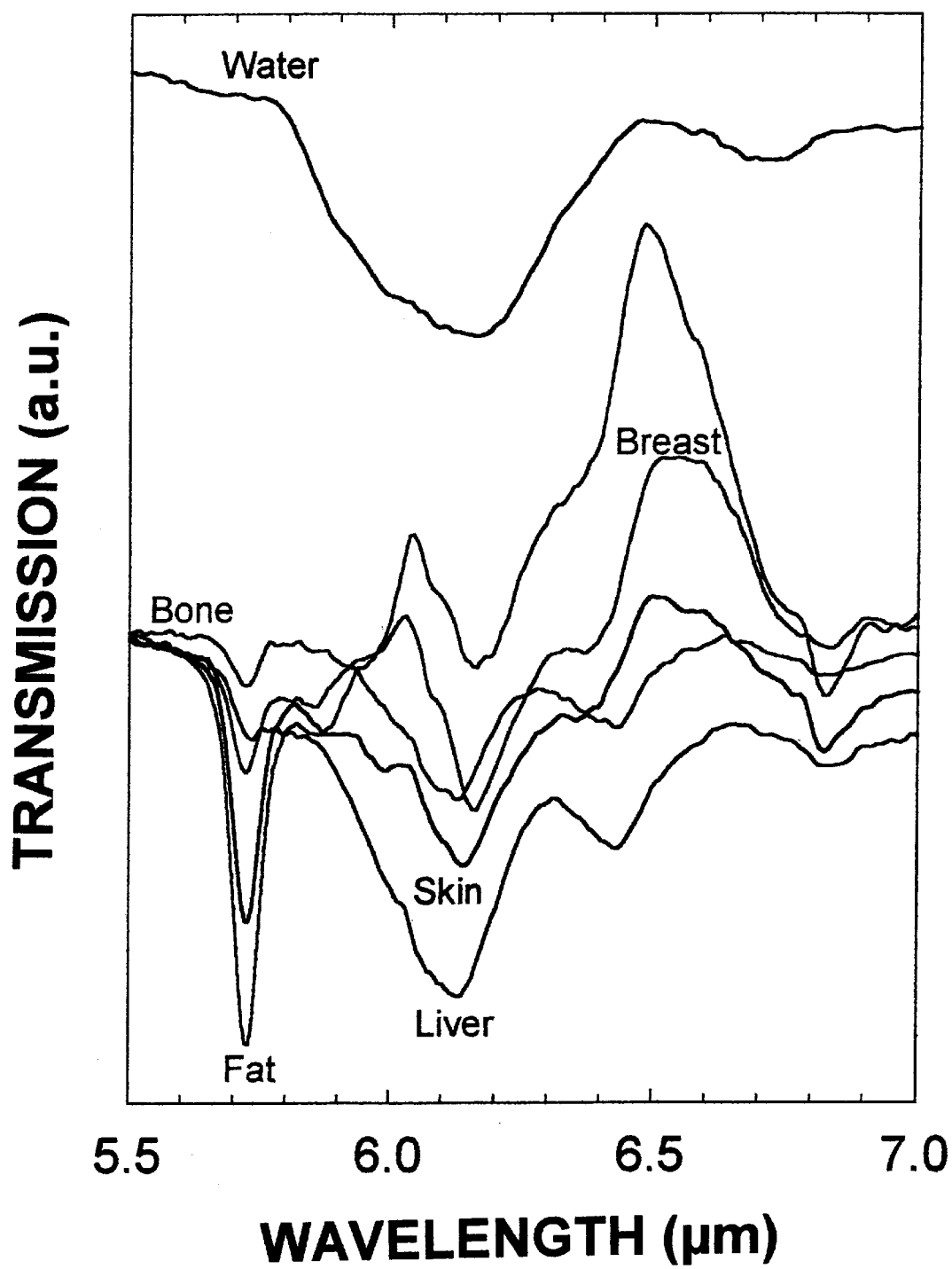
Figure 3C:
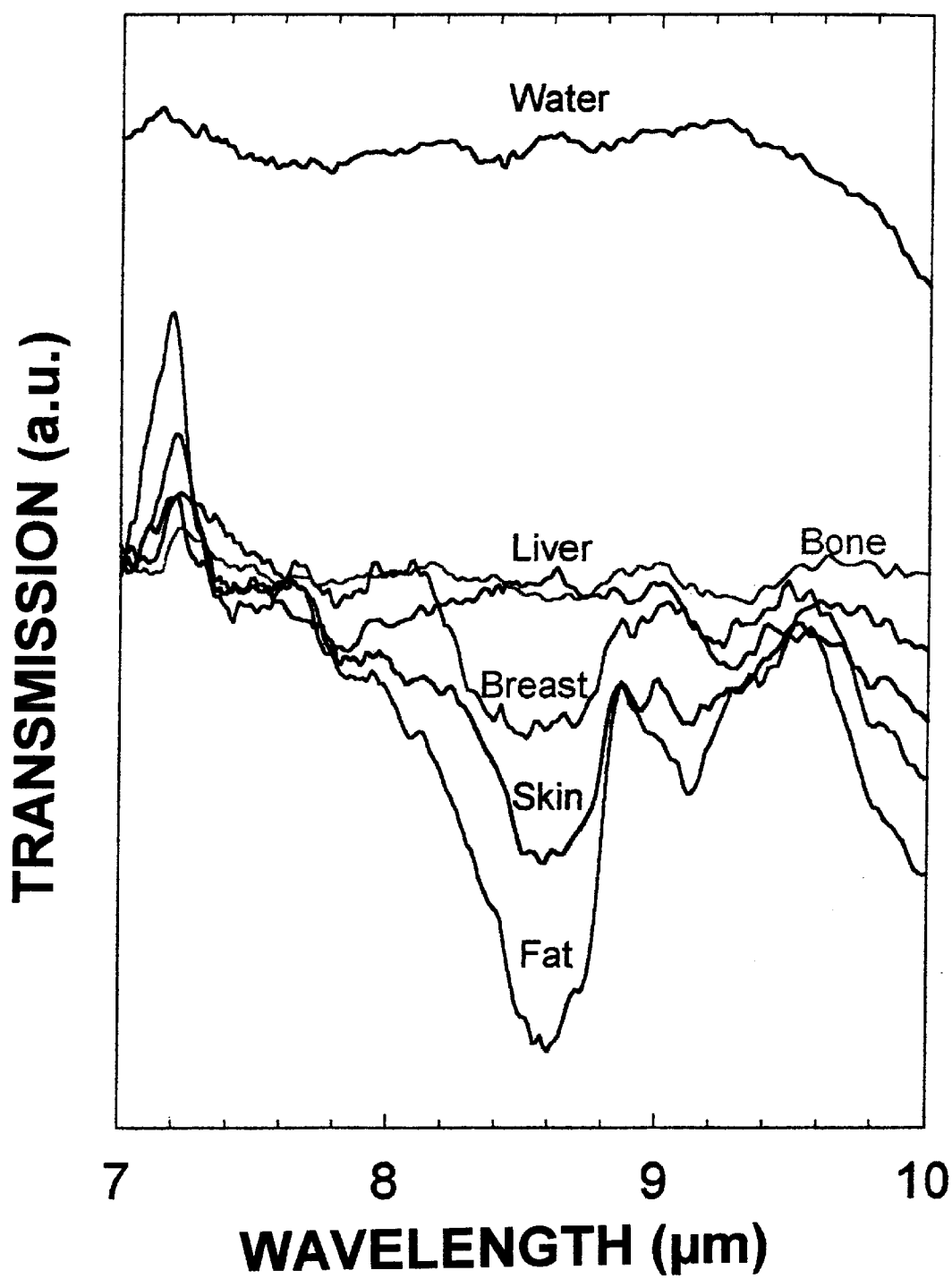

FIG. 2 shows the compilation spectra of all the samples between 2 and 11 microns. FIGS. 3a, b and c show the same data as in FIG. 1 but over the wavelength regions of 2–5 microns, 5.5–7 microns, and 7–10 microns, respectively. The spectra in FIGS. 3a, b and c highlight the differences in chemical characteristics of the various organs and tissues and demonstrate that the fiber is capable of being used for remote spectroscopic characterization of biomedical samples and that water does not mask the infrared spectra. This is highlighted by the observation of the Amide I and Amide II bands between about 6 and 6.6 microns. It is also important to note that the fiber did not break after repeated use.

EXAMPLE 2

Figure 4:
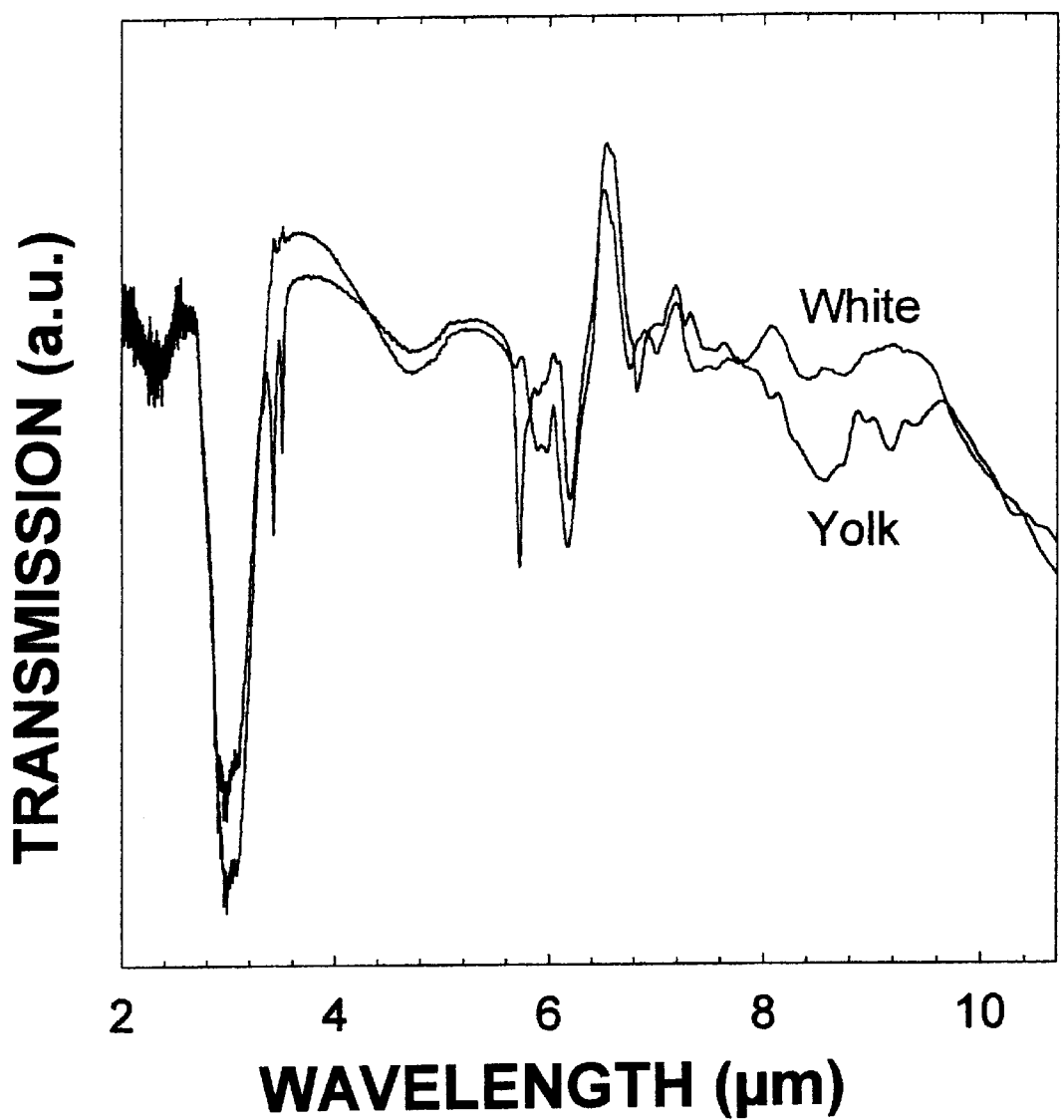
FIG. 4 shows the evanescent spectra of egg white and egg yolk of a chicken egg.

In this example, the setup shown in FIG. 1 was used to record evanescent spectra of a chicken egg white and egg yolk. The fiber used was 1 meter long that had the composition of $Ge_{30}As_{10}Se_{30}Te_{30}$, the same fiber used in Ex. 1. Pursuant to the procedure of this example, the egg white and the egg yolk of a chicken egg were separated and each was separately contacted by the fiber. FIG. 4 shows the evanescent spectra for egg white and yolk. The differences in the egg white and yolk are clearly identifiable and distinguishable based on their characteristic infrared vibrational signatures.

EXAMPLE 3

This example was used to record the evanescent spectrum of human exhaled air using the setup of FIG. 1 and the fiber of Ex. 1.

Figure 5:
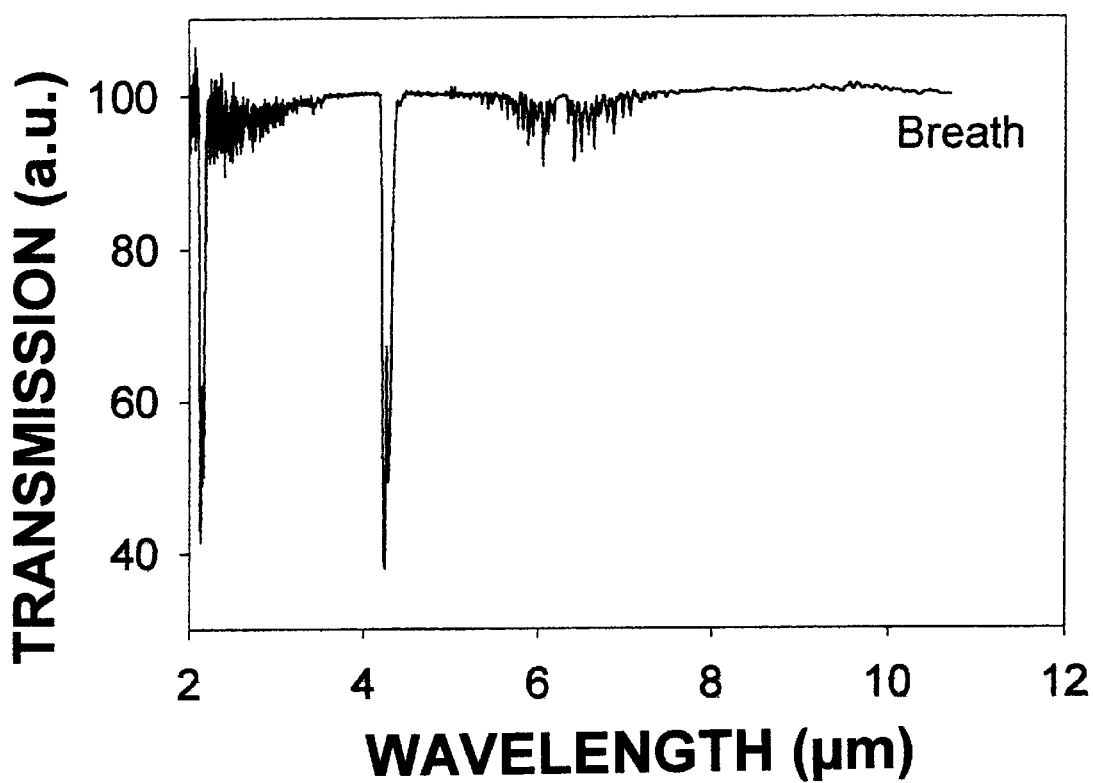
FIG. 5 shows the evanescent spectrum of air exhaled by a person.

Pursuant to the objectives of this example, experimenter exhaled for less than 5 seconds over a small section of the fiber and the spectrum was recorded. FIG. 5 is the evanescent spectrum of the human exhaled air. Carbon dioxide gas is clearly evident in the exhaled breath, based on the infrared absorption band just beyond 4 microns. Bands due to moisture present in the exhaled breath are also evident at about 3 microns and 6 microns.

EXAMPLE 4

This example demonstrates evanescent spectra of a human forearm and the forearm coated with a body lotion, using the setup of FIG. 1 and the fiber of Ex. 1.

Figure 6:
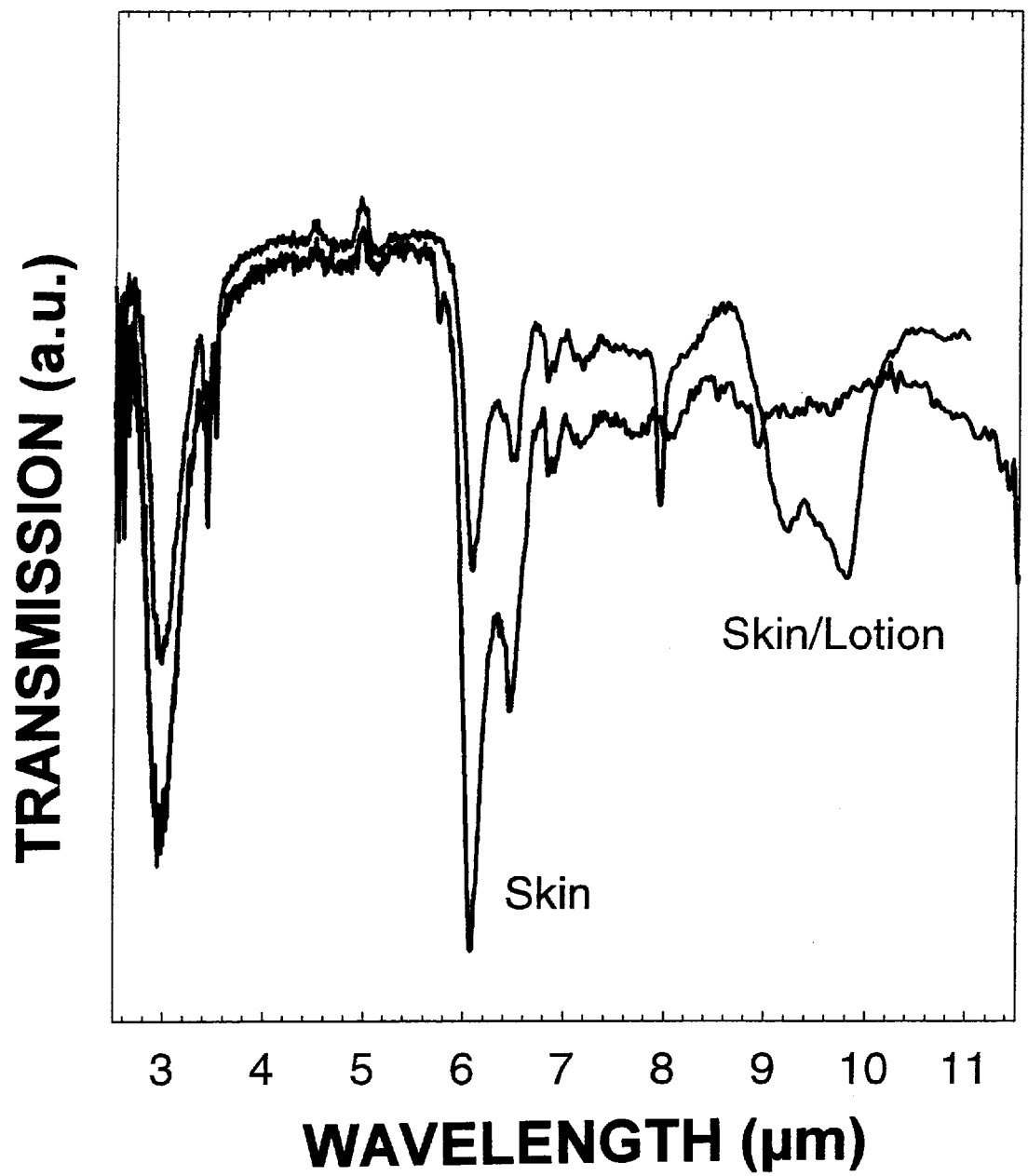
FIG. 6 shows the evanescent spectra of a forearm skin and a generic body lotion applied to the forearm.

Pursuant to the objectives of this example, an experimenter's forearm was placed over the fiber and the spectrum was recorded. For comparison purposes, a generic body lotion was rubbed onto the forearm, the treated forearm was placed over the fiber and the spectrum was also recorded. Results are shown in FIG. 6 where absorption bands due to skin are clearly evident, including the characteristic Amide I and II bands at about 6 and 6.4 microns, respectively. The bands due to the lotion are also clearly discernible, especially at wavelengths beyond 7 microns.

Obviously, many modifications and variations of the present invention are possible in light of the above teachings. It is, therefore, to be understood that, within the scope of the appended claims, the invention may be practiced otherwise than as specifically described.

What is claimed:

1. A method for analyzing a biomedical sample by evanescent spectroscopy comprising the steps of conveying light to a sample through a chalcogenide fiber, conveying light from the sample through a chalcogenide fiber and deriving a spectrum of the sample.

2. The method of claim 1 including the step of introducing light into the input end of the fiber.

3. The method of claim 2 wherein the fiber contains at least 25 mole percent of an element selected from the group consisting of sulfur, selenium, tellurium, and mixtures thereof.

4. The method of claim 3 wherein the sample is non-desiccated flesh.

5. The method of claim 4 wherein the sample is inside a human being.

6. The method of claim 4 wherein the fiber is a cladless multimode fiber in the evanescent coupling region which transmits light in the wavelength range of about 2–12 microns.

7. The method of claim 6 wherein the spectrum is not masked by the presence of water in the sample.

8. The method of claim 4 wherein the sample is human flesh and the fiber transmits light in the wavelength range of about 2–12 microns.

9. The method of claim 8 wherein the fiber is a cladless multimode fiber in the evanescent coupling region which contains at least 50 mole percent of an element selected from the group consisting of sulfur, selenium, tellurium, and mixtures thereof.

10. The method of claim 3 wherein the sample is in vivo.

11. A method for analyzing a biomedical sample comprising the steps of contacting the sample with a chalcogenide glass fiber having input an output ends and light transmitted thereby with some of the light leaving the fiber to form evanescent field, which fiber transmits a signal in response to absorption of some of the light in the evanescent field by the sample; and processing the signal with a Fourier Transform IR Spectrometer to obtain a spectrum which indicates surface character of the sample.

12. The method of claim 11 including the step of introducing light into the input end of the fiber.

13. The method of claim 12 wherein the fiber contains at least 25 mole percent of an element selected from the group consisting of sulfur, selenium, tellurium, and mixtures thereof.

14. The method of claim 13 wherein the sample is non-desiccated flesh.

15. The method of claim 14 wherein the sample is inside a human being.

16. The method of claim 14 wherein the fiber is a cladless multimode fiber which transmits light in the wavelength range of about 2–12 microns.

17. The method of claim 16 wherein the spectrum is not masked by the presence of water in the sample.

18. The method of claim 14 wherein the sample is in vivo human flesh and the fiber transmits light in the wavelength range of about 2–12 microns.

19. The method of claim 18 wherein the fiber is a cladless multimode fiber which contains at least 50 mole percent of an element selected from the group consisting of sulfur, selenium, tellurium, and mixtures thereof.

20. The method of claim 13 wherein the sample is in vivo.

* * * * *